United States Patent [19]

Fleischhaker et al.

[11] Patent Number: 5,114,408
[45] Date of Patent: May 19, 1992

[54] UNIVERSAL HEMOSTASIS VALVE HAVING IMPROVED SEALING CHARACTERISTICS

[75] Inventors: John J. Fleischhaker, Wayzata; Tim T. Hidani, St. Paul, both of Minn.

[73] Assignee: Daig Corporation, Minnetonka, Minn.

[21] Appl. No.: 599,691

[22] Filed: Oct. 18, 1990

[51] Int. Cl.⁵ .................................. A61M 5/178
[52] U.S. Cl. ........................... 604/167; 604/256; 604/905
[58] Field of Search ............... 604/167, 256, 905, 165, 604/164, 169, 168, 201, 86, 88; 251/149.1, 149.2; 137/846, 847, 848, 849, 950

[56] References Cited

U.S. PATENT DOCUMENTS

| | | | |
|---|---|---|---|
| 4,568,336 | 2/1986 | Cooper | 604/905 X |
| 4,842,591 | 6/1989 | Luther | 604/905 |
| 4,909,798 | 3/1990 | Fleischhacker et al. | 604/256 |
| 4,946,133 | 8/1990 | Johnson et al. | 604/256 X |

Primary Examiner—John D. Yasko
Attorney, Agent, or Firm—Donald L. Cox

[57] ABSTRACT

Disclosed herein is a hemostasis valve which is formed of a longitudinally extended valve housing having a first opening and a central longitudinal passage communicating with an opposite second opening. A cap means is provided for enclosing the first opening of the housing, said cap means having a hole to permit insertion of a catheter. Also provided is a one-piece seal means located within the longitudinally extended housing, said seal means comprising a sealing neck having a relatively small opening therein and communicating with a slit concave exit base.

18 Claims, 2 Drawing Sheets

UNIVERSAL HEMOSTASIS VALVE HAVING IMPROVED SEALING CHARACTERISTICS

BACKGROUND OF INVENTION

1. Field of Invention

This invention relates to medical instruments. More particularly, this invention relates to hemostasis valves, or the like which may be used in a wide variety of medical procedures.

2. Prior Art

The introduction of catheters into blood vessels for a variety of purposes such as coronary angiography has been known for many years. Several techniques for introducing these catheters are available. One such technique is the cut-down method. Another is the Seldinger technique. This technique involves surgically opening a vein or artery with a needle, inserting a guidewire into the vessel through the lumen of the needle, withdrawing the needle, inserting over the guidewire a dilator located inside an associated hemostasis valve and sheath, removing the dilator and inserting a catheter through the hemostasis valve and sheath and into the blood vessel.

A wide variety of hemostasis valves are known in the prior art. However, when a guidewire is inserted through most hemostasis valves, because the guidewire is so small relative to the catheters which may also be employed, it is difficult for the valve to seal against the backward pressure of blood, while at the same time permitting easy insertion of much larger diameter catheters. This problem is particularly acute with procedures involving arterial invasion where there is a high reverse pressure of blood. In these arterial procedures, blood can often squirt out when the guidewire is introduced through the hemostasis valve. Excessive blood leakage is viewed by many as extremely dangerous. Most prior art hemostasis valves are designed for use with a particular size of catheter. Because adequate sealing around the catheter walls cannot be obtained for catheters having a range of diameters, it has often not been possible in the past to employ a single hemostasis valve with catheters of widely varying diameters.

In U.S. Pat. No. 4,000,739, the hole (26), is described as being similar in size to the body of the cannula (46) which is introduced into the body. Since, as shown in FIG. 3, the guidewire is several orders of magnitude smaller than the cannula body, any guidewire inserted through the valve is not sealed by the disc (22). While some sealing does occur with the disc (24), the sealing is often not sufficient to stop a reverse flow of blood when only the guidewire is present. Also, because the discs (22) and (24) function independently, it is often possible for the guidewire to move off center of the disc (24), thereby causing a further leakage of blood.

U.S. Pat. No. 4,436,519 discloses a combination of a donut-shaped gasket and a second cup-shaped seal. The device described in the '519 patent is deficient because its donut-shaped gasket can only accept catheters having a relatively limited range of diameters. Moreover, this device is particularly susceptible to leakage when only the guidewire is in place.

The devices described in U.S. Pat. No. 4,673,393, particularly in FIGS. 4 and 5 do not force the centering of the guidewire. Instead, the guidewire may move off-center of the slits and thereby increase the likelihood of a backward flow of blood. A similar problem is seen with the plug described in U.S. Pat. No. 4,610,655 in FIGS. 4 and 5(a).

U.S. Pat. No. 4,655,752 discloses a surgical cannula which again suffers from the deficiency that the first sealing member (79) will not center a guidewire. Moreover, this cannula, like other prior art cannulas, suffers from a lack of universality and from poor sealing. While two seals are employed, the second seal may only be used with catheters having a limited range of diameters and will provide little or no sealing around a guidewire.

U.S. Pat. No. 4,634,432 describes an introducer sheath assembly which contains a single disc (52) having a single slit therein. This disc will permit movement of a guidewire to an off-center position which in turn allows leakage of blood.

U.S. Pat. No. 4,424,833 discloses a gasket assembly in which the opening (48) is large enough to permit a great deal of movement of a guidewire which in turn will permit increased leakage of blood.

U.S. Pat. No. 4,798,594 discloses a hemostasis valve comprised of a plurality of helical slits. Because a pilot or other guiding hole is not present, the guidewire introduced into this valve can readily be skewed off-center, thereby permitting the reverse flow of blood. In a similar fashion, U.S. Pat. No. 4,626,245 describes a valve body containing two Y-shaped slits which are offset one from the other. This offset alignment permits a guidewire inserted into the cannula to move into an off-center position and thereby encourages the reverse leakage of blood.

Another problem shown by many prior art hemostasis cannulas is that the surgeon must be able to "feel" the catheter as it is inserted through the gaskets or other sealing members of the hemostasis unit and ultimately into a blood vessel. If insertion of the catheter through the hemostasis valve is inhibited by friction, the cannula unit may be rejected by surgeons as being difficult to use during catheter insertion. Concomitantly, the use of hemostasis valves which exert undue pressure on the side walls of inserted catheters may lead to excessive hemodynamic dampening of the catheter. In other words, excessive pressure on the exterior side walls of a catheter may cause a narrowing of the catheters diameter thereby altering measurement parameters taken within the catheter.

German Patent No. 3,042,229 purports to describe a hemostasis valve which may be used with catheters having a variety of diameters. However, the sealing means of the device described in the '729 patent is formed from two separate pieces thereby increasing the difficulties of manufacture and the likelihood that one of the seals may become dislodged particularly when large diameter catheters are employed.

Among the prior art hemostasis plug valves or cannulas which offer improvements over prior art devices is included commonly assigned U.S. Pat. No. 4,909,798.

Thus, it is important, in providing a sealing mechanism for a hemostasis valve unit, that the mechanism:

1. Be universal, i.e., useful with both guidewires and with catheters having a wide range of diameters;

2. Provide for relatively easy insertion of all diameters of catheters; and

3. Be free from excessive restriction which would cause hemodynamic dampening.

Accordingly, it is an object of this invention to prepare a hemostasis valve which can effectively seal around both guidewires and cannulas of varying diameters.

It is another object of this invention to prepare a hemostasis valve which is held in the desired position and is not readily displaced by the action of a cannula inserted therethrough.

It is a further object of this invention to prepare a hemostasis valve which will effectively center guidewires to ensure that they do not move to an off-center position, thereby permitting leakage of blood.

It is yet another object of this invention to construct a hemostasis cannula unit which will permit the use of catheters having a wide variety of diameters, while at the same time allowing insertion of any of these catheters without undue pressure/friction thereby providing good surgical "feel" for all diameters of catheters and reduced hemodynamic pressure dampening.

These and other objectives are obtained by utilizing the device described hereafter.

SUMMARY OF INVENTION

This invention involves a hemostasis valve which includes a longitudinally extended housing having first and second opposing ends, a cap means enclosing the first end and having an opening to permit insertion of a dilator or catheter into the longitudinally extended housing and a one-piece seal means located within the central passage of the longitudinally extended housing. The seal means is provided with a sealing neck in communication with a slit disc face which is concave in the direction of the second open end. The second end of the valve housing is attached to a sheath which can be inserted into the vasculature.

By employing this hemostasis valve, it is possible to use catheters which may widely vary in diameter. At the same time surgeons who use the hemostasis valve of the instant invention find that it has excellent "feel" and that hemodynamic pressure dampening is relatively unaffected. Finally, the valve of the instant invention is particularly useful because it provides for good sealing, even around relatively small diameter catheters and guidewires.

The hemostasis cannula unit of the instant invention represents an improvement over the device described in U.S. Pat. No. 4,909,798 in that, because of the concave exit face, the slits in the exit face are maintained in a closed position so as to provide increased sealing against the backward pressure of blood and other body fluids.

DETAILED DESCRIPTION OF INVENTION

Figure 1:
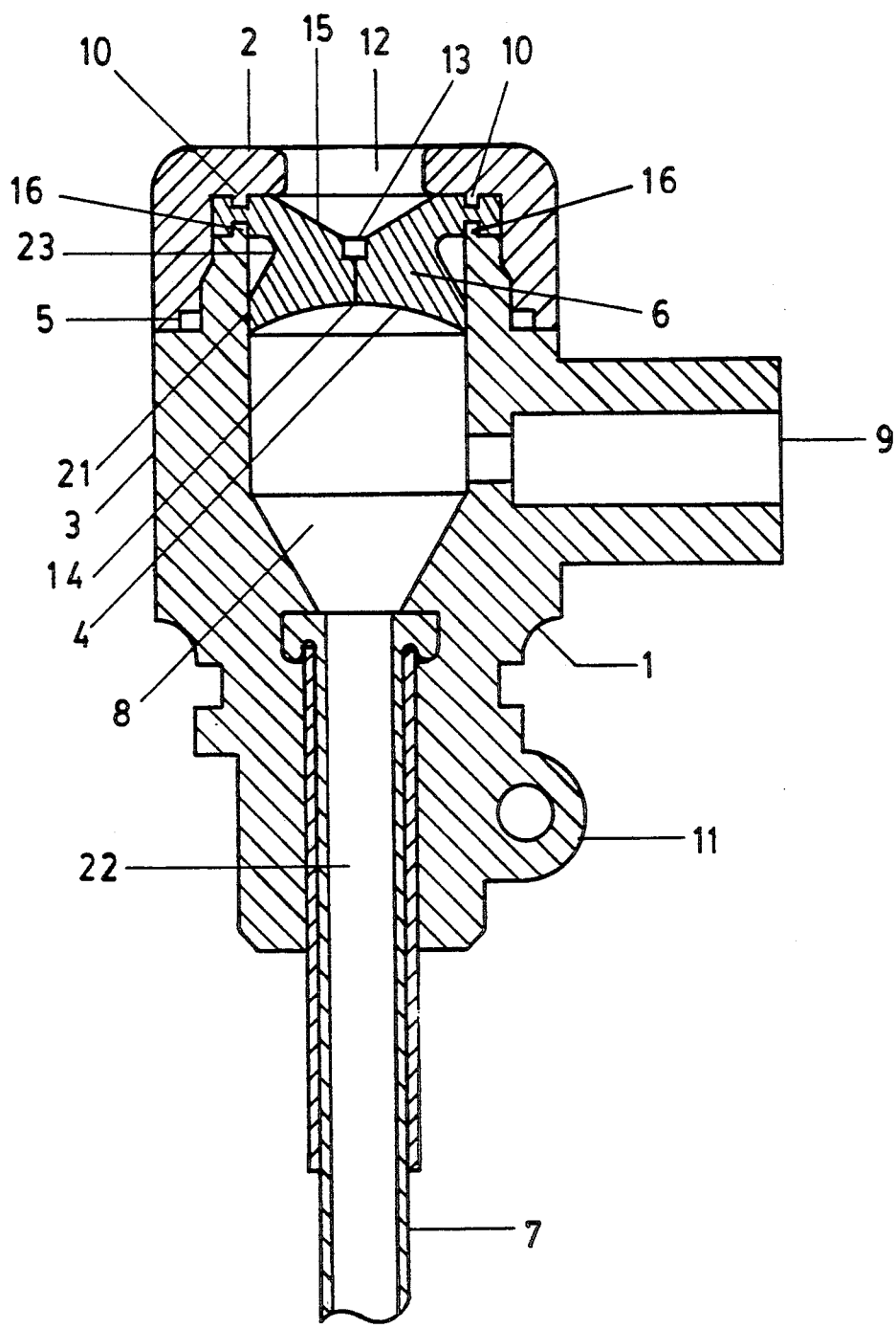
FIG. 1 is a cross-sectional view of the hemostasis valve of the instant invention in place within a hemostasis body/cannula unit assembly.
Figure 1:
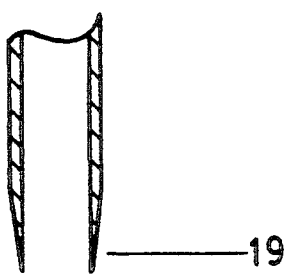

Turning first to FIG. 1 which shows a cross-sectional view of the hemostasis cannula unit of this invention, the cannula unit (1) is formed from four major parts. The first is the cap means (2) which is attached to the top of the longitudinally extended, valve housing (3) and is provided with a first opening (12) which cooperates with a second opposing opening (22) located in the valve housing (3) to permit insertion of a catheter into and out of the interior (8) of the valve housing (3). The cap means (2) and the valve housing (3) are formed from a relatively hard plastic such as a polycarbonate or a polyurethane. The cap means (2) may be secured to the valve housing (3) by mechanically attaching to the housing using threads, clips or, as shown in the drawings, by snap fittings, gluing or welding. The circular groove (5) provides a space for the plastic material from the cap means (2) and the housing (3) to flow into as these materials flow together during the attachment process.

The third major element of the hemostasis cannula unit of the instant invention, the hemostasis valve (6), is formed from a pliant, resilient rubber such as silicone rubber or latex rubber, preferably silicone oil treated silicone rubber, which can be shaped to readily admit passage of catheters. The final major element of the hemostasis cannula unit of the instant invention is a tubular sheath (7) which is formed from a relatively rigid plastic such as teflon or polyethylene. The sheath is inserted within the valve housing (3) and cooperates to provide an exit from the interior of the valve housing (8).

As shown in FIG. 1, the hemostasis valve (6), the cap means (2) and the valve housing (3) are joined together by inserting the valve (6) into the valve housing (3) and then attaching the cap means (2) to the valve housing (3) as previously described, such that the top portion of the valve is in contact with rib (10) of the cap means (2) and rib (16) of the valve housing (3). Preferably ribs (10) and (16) are circular in nature. To hold the valve in place, a circular groove (24) (see FIG. 3) is provided into which the rib (10) is fitted. The cap means (2) may also be provided with a Luer taper (not shown) which can receive corresponding male Luer taper fittings (not shown).

Figure 2:
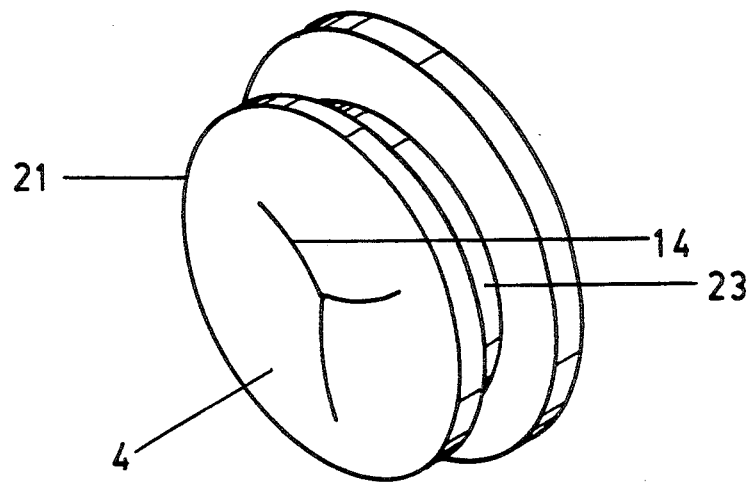
FIG. 2 is a bottom perspective view of the hemostasis valve of the instant invention showing particularly the slit concave exit face.

The valve (6) has a pilot opening (13) in its entry face which leads into the center of a slit (14) which is straight Y, or preferably, curved Y-shaped, as shown in FIG. 2. In addition, the slit (14) may be in the form of a cross or a single slit. Preferably, the pilot opening (13) leads directly to the center of the Y-shaped slit. The diameter of the pilot opening (13) is slightly smaller than the diameter of a guidewire (not shown) which will be used with the hemostasis cannula unit.

The hemostasis valve (6) is also provided with a target receiving area (15) in its entry face to aid in inserting catheters and guidewires. If a catheter is attempted to be inserted slightly off-center, it will readily be guided into the pilot opening (13) and through the slit (14).

The slit (14) is contained in the concave exit face (4) which preferably is maintained in contact with the walls of the valve housing (3). By virtue of the concave nature of the exit face (4) and the fact that the edges (21) of the exit face are in contact with the walls of the valve housing, there is added pressure to maintain the slit in the closed position. In addition, because of the concave nature of the exit face, any backward pressure of blood from the interior (8) of the valve housing (3) will serve to force the slit (14) into its closed position. This pressure continues regardless of whether a cannula or guidewire is inserted through the slit (14).

It is preferred that the valve be provided with a waist (23). As a result, when a catheter is inserted through the pilot opening (13), the adjacent area will not unduly bulge out and come into contact with the walls of valve housing (3). In this way, excess friction upon insertion of large catheters is avoided. Prior art catheters often caused sealing means to expand and contact valve housing walls, thereby increasing friction and pressure on the catheter, making insertion and use more difficult.

The valve housing itself (3) is generally longitudinally extended to form a valve chamber (8) having a second opening (22) opposing the first opening (12) in the cap means (2). This arrangement allows a catheter to be inserted through the cap means (2), and into and out of the valve chamber (8). Preferably access to the interior of the chamber is also provided through a port (9) which facilitates insertion or withdrawal of fluids from the chamber (8).

The valve housing (3) of the hemostasis cannula unit (1) is also provided with a suture loop (11) to allow temporary attachment directly to a patient's body to provide stabilization of the hemostasis cannula unit.

The final element of the hemostasis cannula unit of the instant invention is the sheath (7) onto which the valve housing (3) may be attached. The sheath preferably is provided with a tapered distal tip (19) which in the preferred use closely fits onto a dilator which is inserted through the cannula for initial introduction into a blood vessel.

FIG. 2 provides a perspective view from the point of view of the concave exit face (4). The edge (21) of the concave exit face (4) which is in contact with the interior surface of the valve housing (8) is also shown as is a curved Y-shaped slit (14). Also shown is the waist (23).

Figure 3:
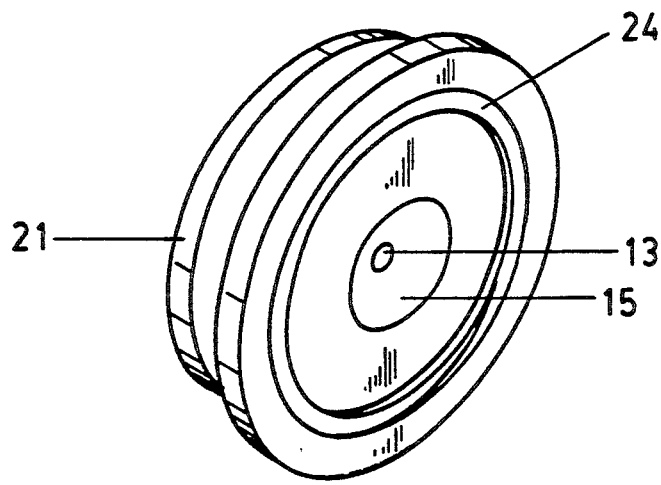
FIG. 3 is a top perspective view of the hemostasis valve of the instant invention showing the entry face of the hemostasis valve.

FIG. 3 is a top perspective view of the valve of the instant invention from the point of view of the entry face. The pilot opening (13) is shown as is the target receiving area (15). Also shown is a circular groove (24) which receives the rib (10).

In the preferred means of operation, a needle is inserted into a patient's blood vessel. Through the lumen of the needle a guidewire is in turn inserted into the blood vessel. The hemostasis cannula unit of the instant invention is then prepared by inserting a dilator through the first opening (12), the valve (6), out the second opening (22), through the sheath (7), and out the tapered distal tip (19). The sheath (7) and dilator are designed such that the tapered distal tip (19) snugly fits around the dilator.

Once the needle is removed leaving only the guidewire protruding from the patient, the dilator and hemostasis cannula unit are advanced together onto the guidewire and into the blood vessel. The dilator tip, which is tapered, gradually increases the size of the opening in the blood vessel as it enters the vessel. Sheath (7) continues to increase the opening in the vessel as it is further inserted. After the sheath is inserted into the blood vessel, the dilator is removed, leaving in place the hemostasis cannula unit of the instant invention with the guidewire protruding therefrom, sealed by the pilot opening (13) and the slit (14).

A catheter may then be inserted through the first opening (12) in the cap means (2), into the valve (6) through the pilot opening (13) and out the slit (14). After exiting the slit (14), the catheter is advanced out the second opening (22) down through the sheath (7) and into the blood vessel. Any blood which flows between the sheath and the catheter and up into the interior of the valve body (8) is not permitted to escape to the exterior because of the strong sealing action of pilot opening (13) acting in concert with the concave exit face (4) and the slits (14).

The hemostasis valve of the instant invention provides several advantages not found in prior art sealing valves. A major advantage of the valve of the instant invention is that, because of its one-piece nature, there is a significantly reduced possibility for blood clots to form within the valve itself. Many prior art hemostasis valves are constructed utilizing multiple components placed in face-to-face or nearly face-to-face proximity. However, small clots can easily accumulate between these component faces. The valve of the instant invention, on the other hand, does not permit the accumulation of blood within its structure.

Another major problem faced by hemostasis cannulas of the prior art is that they are unable to effectively seal around guidewires. Moreover, many of the prior art hemostasis valves permit guidewires to be displaced toward the edge of slitted valve bodies. The structure of the instant invention limits displacement of this type and at the same time reduces or eliminates the possibility of air aspiration. Because the guidewire is held in place by the pilot opening, it cannot readily be displaced to the side into one of the arms of the slit. The hemostasis valve of the instant invention also finds particular importance because, unlike prior art hemostasis valves, it provides effective sealing action against high pressure arterial blood, even when only a guidewire is in place.

Another important feature of the hemostasis valve of the instant invention is that it provides the required feel characteristics and permits the use of catheters having a wide variety of external diameters. Many prior hemostasis valves are useful only for a relatively small range of catheter diameters. However, because of the design of the instant invention, it is possible to utilize a wide range of catheters having a relatively large range of diameters.

The present embodiment of the instant invention is considered to be merely illustrative and changes may be made in its specific form without departing from the spirit or essential characteristics of this invention.

We claim:

1. A hemostasis cannula unit comprising:
  (a) a longitudinally extended valve housing having a first opening and a central longitudinal chamber communicating with a second opening;
  (b) a cap means enclosing the first opening of the valve housing and providing a hole to permit the insertion of a catheter into the housing's first opening through the central chamber and out the second opening; and
  (c) a one-piece seal means stationarily located within said central chamber and having an entry face containing a conical receiving area tapered into a pilot opening wherein said entry face is in contact with a slit concave exit face.

2. The hemostasis cannula unit of claim 1 wherein the valve housing includes an exit port providing access to the central chamber.

3. The hemostasis cannula unit of claim 1 wherein the edges of the slit concave exit face are in contact with the walls of the valve housing.

4. The hemostasis cannula unit of claim 1 wherein the seal means is provided with a waist area adjacent to the pilot opening.

5. The hemostasis cannula unit of claim 1 in combination with a sheath means.

6. The hemostasis cannula unit of claim 5 wherein the sheath means is tapered at the distal end.

7. The hemostasis cannula unit of claim 1 wherein the slit in the exit face is Y-shaped.

8. The hemostasis cannula unit of claim 1 wherein the slit in the exit face is aligned with the pilot opening.

9. A one-piece hemostasis valve seal means for location within the passage of a hemostasis valve housing comprising an entry face containing a receiving area leading to a pilot opening wherein said entry face is in contact with a slit concave exit face wherein the slit is maintained in a closed position in the presence of arterial blood pressure.

10. The valve seal means of claim 9 wherein said seal means is provided with a waist area adjacent to the pilot opening.

11. The seal means of claim 9 wherein the slit is Y-shaped.

12. The seal means of claim 9 wherein the slit in the exit face is aligned with the pilot opening.

13. A hemostasis cannula unit comprising:
(a) a longitudinally extended valve housing having a first opening and a central longitudinal chamber communicating with a second opening;
(b) a cap means enclosing the first opening of the valve housing and providing a hole to permit the insertion of a catheter into the housing's first opening through the central chamber and out the second opening; and
(c) a one-piece seal means stationarily located within said central chamber and having an entry face containing a conical receiving are tapered into a pilot opening which communicates with a slit concave exit face wherein the edges of the slit concave exit face are in contact with the walls of the valve housing.

14. The hemostasis cannula unit of claim 13 wherein the seal means is provided with a waist area adjacent to the pilot opening.

15. The hemostasis cannula unit of claim 13 in combination with a sheath means.

16. The hemostasis cannula unit of claim 15 wherein the sheath means is tapered at the distal end.

17. The hemostasis cannula unit of claim 13 wherein the slit in the exit face is Y-shaped.

18. The hemostasis cannula unit of claim 13 wherein the slit in the exit face is aligned with the pilot opening.

* * * * *